US012685296B2

(12) United States Patent
Zhang et al.

(10) Patent No.: US 12,685,296 B2
(45) Date of Patent: Jul. 21, 2026

(54) INDIRECT SELECTIVE BREEDING METHOD OF HIGH-COLLAGEN MEAT GEESE

(71) Applicant: YANGZHOU UNIVERSITY, Yangzhou (CN)

(72) Inventors: Yu Zhang, Yangzhou (CN); Qi Xu, Yangzhou (CN); Yang Zhang, Yangzhou (CN); Zhengfeng Cao, Yangzhou (CN); Wangyang Ji, Yangzhou (CN); Zhixiu Wang, Yangzhou (CN); Guohong Chen, Yangzhou (CN); Wenming Zhao, Yangzhou (CN)

(73) Assignee: YANGZHOU UNIVERSITY, Yangzhou (CN)

( * ) Notice: Subject to any disclaimer, the term of this patent is extended or adjusted under 35 U.S.C. 154(b) by 923 days.

(21) Appl. No.: 17/924,687

(22) PCT Filed: May 26, 2022

(86) PCT No.: PCT/CN2022/095132
§ 371 (c)(1),
(2) Date: Dec. 29, 2022

(87) PCT Pub. No.: WO2022/267807
PCT Pub. Date: Dec. 29, 2022

(65) Prior Publication Data
US 2023/0354789 A1 Nov. 9, 2023

(30) Foreign Application Priority Data
Jun. 23, 2021 (CN) .......................... 202110698218.9

(51) Int. Cl.
*A01K 67/02* (2006.01)
*G06F 17/18* (2006.01)

(52) U.S. Cl.
CPC .............. *A01K 67/02* (2013.01); *G06F 17/18* (2013.01); *A01K 2227/30* (2013.01)

(58) Field of Classification Search
None
See application file for complete search history.

(56) References Cited

U.S. PATENT DOCUMENTS

| | | | |
|---|---|---|---|
| 5,944,652 A | 8/1999 | Miller et al. |
| 6,440,666 B1 | 8/2002 | Groenen et al. |
| 2020/0100480 A1 | 4/2020 | Doran et al. |

FOREIGN PATENT DOCUMENTS

| | | |
|---|---|---|
| CN | 102696544 A | 10/2012 |
| CN | 105891432 A | 8/2016 |
| CN | 105981690 A | 10/2016 |
| CN | 106489831 A | 3/2017 |
| CN | 106857398 A | 6/2017 |
| CN | 106937622 A | 7/2017 |
| CN | 109287566 A | 2/2019 |
| CN | 109757435 A | 5/2019 |
| CN | 109952997 A | 7/2019 |
| CN | 113317275 A | 8/2021 |
| SU | 1762830 A1 | 9/1992 |

OTHER PUBLICATIONS

DB3210/T 1048-2020, Technical regulation of feeding and management for breeder Yangzhou geese, Yangzhou Local Standards, 2020, pp. 1-9, Yangzhou Market Supervision and Administration Bureau.

*Primary Examiner* — Peter Paras, Jr.
*Assistant Examiner* — Khoa Nhat Tran
(74) *Attorney, Agent, or Firm* — Birchwood IP

(57) ABSTRACT

An indirect selective breeding method of high-collagen meat geese includes: (1) obtaining a curve equation y=0.017x+0.026; (2) rearing goslings to young geese; (3) measuring the length, width, and height values of the knobs of the geese, and calculating to give the collagen content according to the curve equation obtained in step (1); (4) sorting the geese in descending order according to the collagen content and keeping the geese with collagen content ranked top 50% as breeding geese; (5) after the geese lay eggs, hatching the goose eggs into goslings; and (6) repeating steps (2)-(5) for selective breeding over generations. The indirect selective breeding method is simple and easy to implement. A new strain of meat geese with high collagen content can be obtained from selective breeding simply by measuring the length, width, and height of the knobs of geese of each generation.

8 Claims, 1 Drawing Sheet

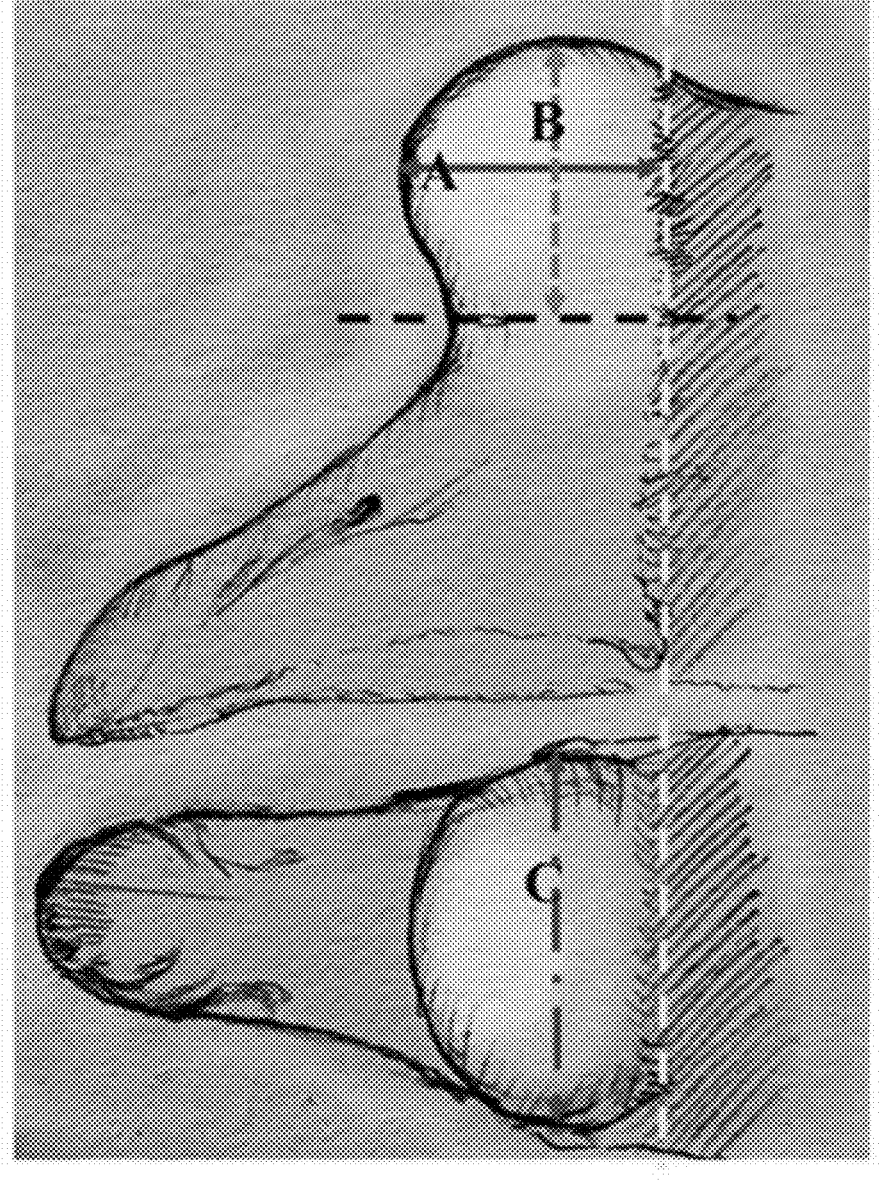

INDIRECT SELECTIVE BREEDING METHOD OF HIGH-COLLAGEN MEAT GEESE

CROSS REFERENCE TO THE RELATED APPLICATIONS

This application is the national phase entry of International Application No. PCT/CN2022/095132, filed on May 26, 2022, which is based upon and claims priority to Chinese Patent Application No. 202110698218.9, filed on Jun. 23, 2021, the entire contents of which are incorporated herein by reference.

TECHNICAL FIELD

The present invention relates to an indirect selective breeding method of high-collagen meat geese, and relates to the technical field of selective breeding of livestock.

BACKGROUND

Collagen has the function of maintaining the form and structure of skin, tissues and organs. It is also an important raw material substance for repairing tissue damage, and plays an important role in maintaining the elasticity of skin and preventing wrinkles and relaxation. Collagen in meat is one of the main sources of collagen intake, but the collagen content of meat is generally low, only 0.3%-1.5%. Geese are birds with high collagen content. They are consumed as the main source of collagen supplement in Guangdong and other regions. In such contexts, how to increase the collagen content in muscle by means of selective breeding has become one of the problems in urgent need of solutions in meat goose husbandry. However, the collagen content in muscle is a trait that cannot be determined in living animals, and, as a result, effective selective breeding has been prevented from being carried out.

Knobs, as a typical sign on the forehead of Chinese geese, are also a secondary sexual characteristic of geese in appearance. To date, little attention has been paid to the genetic characteristics of the knob. At present, it is only known that the knob is incompletely dominant, and that adult geese always have a larger knob than immature ones. As for the relationship between the knob size and production performances such as meat quality, no related studies have been reported.

SUMMARY

Objective: The present invention is intended to provide an indirect selective breeding method of high-collagen meat geese.

Technical solutions: The present invention discloses an indirect selective breeding method of high-collagen meat geese, comprising the following steps:

(1) measuring length, width and height of knobs of young geese, determining collagen content in leg muscle of the corresponding geese, and performing linear fitting on knob size, i.e., the length×the width×the height, and the collagen content in leg muscle to obtain a linear curve equation between the knob size of the geese and the collagen content in muscle: y=0.017x+0.026;

(2) rearing goslings to young geese;

(3) measuring length, width and height of knobs of the young geese, and calculating to give collagen content in leg muscle of the geese according to the curve equation obtained in step (1);

(4) sorting the geese in descending order according to the collagen content and keeping male geese and female geese with collagen content in leg muscle ranked top 50% as breeding geese to form a family line;

(5) after the female breeding geese lay eggs, hatching the goose eggs into goslings; and (6) repeating steps (2)-(5) for selective breeding over generations to obtain high-collagen meat geese.

Furthermore, the young geese have a breeding age of 120-150 days.

Furthermore, the geese are Yangzhou geese or new strains of Yangzhou goose lineage.

Furthermore, in step (1), the linear fitting is performed by SPSS19.0 linear regression; the number of the young geese is greater than 60, and the ratio of male geese to female geese is 1:1. Furthermore, in step (2), the rearing is performed under conditions of ground-rearing or net-rearing with ad libitum access to food and water and with natural lighting.

Furthermore, in step (3), the number of the breeding geese is 40-80 family lines that each comprise 1 male goose and 5-6 female geese.

Furthermore, in step (5), the goose eggs to be hatched into goslings are eggs laid by female breeding geese aged 44-46 weeks.

Furthermore, in the step (6), the selective breeding over generations is selective breeding over 3-5 generations.

To date, little attention has been paid to the genetic characteristics of the knob, a secondary sexual characteristic of a goose in appearance. In the present invention, through numerous measurements of indicators of knob size and meat quality traits (protein content in muscle, fat content in muscle, collagen content in muscle and the like), a linear relationship is found between the knob size and the collagen content in muscle for the first time—that is, the larger the knob, the higher the collagen content in muscle. Therefore, the indicator of knob size can be utilized to indirectly select the meat geese with high collagen content in muscle for breeding.

Beneficial effects: The present invention has the following remarkable advantages over the prior art:

(1) In the present invention, on the basis of numerous measurements in the early stage, the knob size is found significantly correlated with the collagen content in muscle by Pearson correlation analysis, and a linear relationship y=0.017x+0.026 is found between the knob size and the collagen content in muscle of geese by further linear regression analysis.

(2) The selective breeding method disclosed herein is simple and easy to implement. A new strain of meat geese with high collagen content can be obtained from selective breeding simply by measuring the length, width and height of the knobs of meat geese after goslings are reared to young geese.

(3) The results of the selective breeding method disclosed herein are accurate and reliable. The collagen content in muscle can be effectively increased by more than 20% through the implementation of this technique.

BRIEF DESCRIPTION OF THE DRAWING

FIGURE is a schematic diagram showing the measurement of the length, width and height values of a knob of a goose according to the present invention.

DETAILED DESCRIPTION OF THE EMBODIMENTS

The technical solutions of the present invention are further illustrated below with reference to the accompanying drawing.

Example 1

(1) The length (vertical length from the most anterior end of the knob to the junction between the knob skin and the feather-covered area in mm with 1 decimal place), the width (maximum width between both sides of the knob in mm with 1 decimal place), and the height (vertical length from the top end of the knob to the junction between the nose and forehead in mm with 1 decimal place) of the knobs of 180 male Yangzhou geese aged 120 days were measured specifically as shown in FIGURE, which is a schematic diagram showing the measurement of the length, width and height of a knob of a goose according to the present invention and in which A is the length of the knob, B is the width of the knob, and C is the height of the knob. The knob size was then calculated (length×width×height, in cm$^3$). Meanwhile, the collagen content in leg muscle, the protein content in leg muscle and the fat content in leg muscle of the corresponding male Yangzhou geese were also determined by a FOSS FoodScan Meat Analyzer, and the results are shown in Table 1. Pearson correlation analysis was performed using the SPSS19.0 software on knob size and collagen content in leg muscle, on knob size and protein content in leg muscle, and on knob size and fat content in leg muscle. The results are shown in Table 2.

TABLE 1

Length, width, height of knobs and knob size as well as collagen content in leg muscle of some male Yangzhou geese

| Length of knob (mm) | Width of knob (mm) | Height of knob (mm) | Knob size (cm$^3$) | Collagen content in leg muscle (%) | Protein content in leg muscle (%) | Fat content in leg muscle (%) |
|---|---|---|---|---|---|---|
| 19.8 | 31.9 | 12.9 | 8.15 | 0.19 | 21.23 | 4.44 |
| 18.7 | 32.1 | 24.4 | 14.65 | 0.28 | 21.95 | 4.52 |
| 22.5 | 30.0 | 23.0 | 15.53 | 0.31 | 21.51 | 3.09 |
| 21.0 | 34.0 | 24.0 | 17.14 | 0.29 | 21.05 | 4.25 |
| 26.0 | 31.0 | 28.0 | 22.57 | 0.35 | 21.56 | 3.07 |
| 27.1 | 34.7 | 25.6 | 24.07 | 0.48 | 22.28 | 1.71 |
| 23.7 | 34.2 | 31.8 | 25.78 | 0.50 | 21.53 | 2.72 |
| 31.8 | 34 | 27 | 29.192 | 0.59 | 20.25 | 4.48 |
| 28.2 | 33.7 | 32.2 | 30.592 | 0.56 | 20.29 | 4.55 |

TABLE 2

Correlation analysis of knob size with collagen content, protein content and fat content in muscle

| Traits | Collagen content in leg muscle | Protein content in leg muscle | Fat content in leg muscle |
|---|---|---|---|
| Correlation coefficient | 0.954** | −0.467 | 0.063 |

In this table, ** indicates extremely significant correlation between traits.

It can be found from Table 2 that the knob size is only significantly correlated with the collagen content in muscle, but not with the protein content in leg muscle or the fat content in leg muscle. Linear regression was further adopted to perform linear fitting on the knob size (length×width×height, in cm$^3$) and the collagen content in leg muscle, a linear relationship equation y=0.017x+0.026 was obtained, where y represents the collagen content in leg muscle (%), and x represents the knob size (cm$^3$). The linear coefficient R2 of the resulting equation was 0.9105, and the chi-square $\chi^2$ fit test revealed no significant difference between the prediction results and the experimental results, indicating that the resulting equation is entirely applicable to predicting the collagen content in leg muscle of Yangzhou geese aged 120 days. That is, the larger the knob, the higher the collagen content in muscle. Therefore, the indicator of knob size can be utilized to indirectly select the meat geese with high collagen content in muscle for breeding.

(2) Under conditions of ground-rearing with ad libitum access to unlimited feed and with natural lighting, over 1000 breeding Yangzhou geese were reared to the age of 120 days according to the rearing standard for breeding Yangzhou goose DB3210/T 1048-2020.

(3) The length, width and height of the knobs of the Yangzhou goose individuals were measured separately using a vernier caliper at the age of 120 days, specifically as shown in FIGURE. The knob size (length×width×height, in cm$^3$) of the meat goose individuals was calculated, and their foot numbers were recorded. Table 3 lists the measurement results of the length, width, height of knobs and the knob size of some of the Yangzhou geese aged 120 days.

TABLE 3

The length, width, height of knobs and the knob size of some of the Yangzhou geese aged 120 days

| Meat goose No. | Length of knob (mm) | Width of knob (mm) | Height of knob (mm) | Knob size (cm$^3$) |
|---|---|---|---|---|
| 1901 | 23.5 | 35.0 | 25.1 | 20.645 |
| 1904 | 30.0 | 38.0 | 29.5 | 33.630 |
| 1908 | 23.0 | 32.2 | 28.0 | 20.737 |
| 1909 | 26.0 | 31.0 | 28.0 | 22.568 |
| 1916 | 21.0 | 34.0 | 24.0 | 17.136 |
| 1921 | 26.0 | 32.5 | 26.0 | 21.970 |
| 1925 | 26.5 | 35.0 | 32.0 | 29.680 |
| 1932 | 30.3 | 34.0 | 28.0 | 28.846 |
| 1936 | 30.0 | 33.5 | 33.1 | 33.266 |
| 1942 | 22.5 | 30.0 | 23.0 | 15.525 |
| 1951 | 31.8 | 34.0 | 27.0 | 29.192 |
| 1964 | 28.2 | 33.7 | 32.2 | 30.595 |
| 1979 | 25.0 | 33.0 | 28.4 | 23.430 |
| 1988 | 22.0 | 30.0 | 26.0 | 17.160 |

(4) The expected collagen content in leg muscle of each goose was calculated according to the equation y=0.017x+0.026.

(5) The meat geese were sorted in descending order according to the collagen content in leg muscle, and meat geese with collagen content greater than or equal to 0.424%, i.e. the meat geese ranked top 50%, were kept as breeding geese. As shown in Table 4, the geese meeting the requirements for collagen content calculated on the basis of Table 3 were kept as breeding geese, and their foot numbers were 1904, 1925, 1932, 1936, 1951, 1964 and 1979.

TABLE 4

Meat goose individuals kept based on collagen content in leg muscle

| Meat goose No. | Sex | Knob size (cm³) | Calculated collagen content (%) | Kept or not |
|---|---|---|---|---|
| 1901 | ♂ | 20.645 | 0.377 | |
| 1904 | ♀ | 33.630 | 0.598 | √ |
| 1908 | ♀ | 20.737 | 0.379 | |
| 1909 | ♂ | 22.568 | 0.410 | |
| 1916 | ♀ | 17.136 | 0.317 | |
| 1921 | ♂ | 21.970 | 0.399 | |
| 1925 | ♂ | 29.680 | 0.531 | √ |
| 1932 | ♀ | 28.846 | 0.516 | √ |
| 1936 | ♀ | 33.266 | 0.592 | √ |
| 1942 | ♀ | 15.525 | 0.290 | |
| 1951 | ♂ | 29.192 | 0.522 | √ |
| 1964 | ♀ | 30.592 | 0.546 | √ |
| 1979 | ♂ | 23.430 | 0.424 | √ |
| 1988 | ♀ | 17.160 | 0.318 | |

(6) After the breeding geese had been reared to the age of 180 days, the geese with foot numbers 1904, 1925, 1932, 1936, 1951, 1964 and 1979 in Table 4 were kept as breeding geese to form a family line; and the eggs laid by the female breeding geese at the age of 44-46 weeks were hatched.

(7) After the goslings were hatched out, steps (2)—(6) were repeated to carry out selective breeding for generation 1, and then steps (2)—(6) were repeated again to carry out selective breeding for generation 2 and generation 3. The selective breeding results are shown in Table 5. Table 5 lists the theoretical results calculated according to the equation y=0.017x+0.026 and the actual results after selective breeding over 3 generations using the selective breeding method of the present invention.

TABLE 5

Theoretical and measured collagen content in leg muscle of meat geese of selective breeding over 3 generations

| | Generation 0 | Generation 1 | Generation 2 | Generation 3 |
|---|---|---|---|---|
| Knob size at the age of 120 days (cm³) | 23.34 | 24.81 | 26.73 | 29.02 |
| Average value of calculated collagen content (%) | 0.423 | 0.448 | 0.480 | 0.519 |
| Average value of actual collagen content (%) | 0.410 | Not measured | Not measured | 0.506 |

As can be seen from Table 5, the collagen content in leg muscle of the candidate goose population was significantly increased by using the method disclosed herein for 3 generations of selective breeding, and the collagen content of this strain was significantly genetically improved. The collagen content in leg muscle of the geese aged 120 days reached 0.506%, which was 23.41% higher than that in generation 0. The problem that living animals cannot be directly selected by muscle collagen was well solved by indirect selection by knob size.

What is claimed is:

1. An indirect selective breeding method of high-collagen meat geese, comprising:

(1) measuring first lengths, first widths, and first heights of first knobs of first young geese, determining a first collagen content in a first leg muscle of the first young geese, and performing a linear fitting on a size, of the first length×the first width×the first height of the first knobs and the first collagen content in first leg muscle to obtain a linear equation between the size and the first collagen content in the first leg muscle: y=0.017x+ 0.026, wherein y is collagen content, x is the size of the knobs, that is the first length >the first width >the first height of the first knobs;

(2) rearing first goslings to second young geese;

(3) measuring lengths, widths, and heights of second knobs of second young geese, and conducting a calculation according to the linear equation obtained in step (1) to give a second collagen content in a second leg muscle of the second young geese;

(4) sorting the second young geese in a descending order according to the second collagen content and selecting male geese and female geese with the second collagen content ranked a top 50% as breeding geese to form a family line;

(5) after the female geese in step (4) lay eggs, hatching the eggs into second goslings; and (6) repeating steps (2)-(5) for a selective breeding over generations to obtain the high-collagen meat geese.

2. The indirect selective breeding method of the high-collagen meat geese according to claim 1, wherein the first young geese and the second young geese have a breeding age of 120 days-150 days.

3. The indirect selective breeding method of the high-collagen meat geese according to claim 1, wherein the high-collagen meat geese are Yangzhou geese.

4. The indirect selective breeding method of the high-collagen meat geese according to claim 1, wherein in the step (1), the linear fitting is performed by linear regression analysis, and a number of the first young geese is more than 60.

5. The indirect selective breeding method of the high-collagen meat geese according to claim 1, wherein in the step (2), the rearing is performed under conditions of a ground-rearing or a net-rearing with an ad libitum access to a food and a water and with a natural lighting.

6. The indirect selective breeding method of the high-collagen meat geese according to claim 1, wherein in the step (4), there are 40-80 family lines of breeding geese, each family line of breeding geese comprises 1 male goose and 5-6 female geese.

7. The indirect selective breeding method of the high-collagen meat geese according to claim 1, wherein in the step (5), the eggs to be hatched into the second goslings are laid by the female geese aged 44 weeks-46 weeks.

8. The indirect selective breeding method of the high-collagen meat geese according to claim 1, wherein in the step (6), the selective breeding is performed for 3 to 5 generations, and the geese of the 3rd to 5th generations are obtained as the high-collagen meat geese.

* * * * *